(12) United States Patent
Stolarski et al.

(10) Patent No.: US 9,056,011 B2
(45) Date of Patent: Jun. 16, 2015

(54) DISPOSABLE ORTHOPEDIC PROSTHESIS MOLD

(75) Inventors: Edward Stolarski, Sarasota, FL (US); James Scott Hay, Parkland, FL (US); Julius Garcia, Lauderhill, FL (US)

(73) Assignee: OSM Medical Products, LLC, Delray Beach, FL (US)

( * ) Notice: Subject to any disclaimer, the term of this patent is extended or adjusted under 35 U.S.C. 154(b) by 274 days.

(21) Appl. No.: 13/441,089

(22) Filed: Apr. 6, 2012

(65) Prior Publication Data
US 2012/0256344 A1    Oct. 11, 2012

Related U.S. Application Data

(60) Provisional application No. 61/472,498, filed on Apr. 6, 2011.

(51) Int. Cl.
*A61F 2/30* (2006.01)
*A61F 2/38* (2006.01)

(52) U.S. Cl.
CPC ........... *A61F 2/30942* (2013.01); *A61F 2/3859* (2013.01); *A61F 2/389* (2013.01); *A61F 2002/3071* (2013.01); *A61F 2002/30957* (2013.01); *A61F 2/3094* (2013.01); *A61F 2002/30617* (2013.01); *A61F 2002/30672* (2013.01); *A61F 2310/00353* (2013.01)

(58) Field of Classification Search
USPC ........ 264/251; 623/901; 249/55, 61, 141, 168
See application file for complete search history.

(56) References Cited

U.S. PATENT DOCUMENTS

| 3,907,245 | A |   | 9/1975  | Linder |
| 3,990,672 | A | * | 11/1976 | Buchanan ...................... 249/48 |
| 5,123,927 | A |   | 6/1992  | Duncan et al. |
| 5,236,457 | A |   | 8/1993  | Devanathan |
| 5,538,514 | A |   | 7/1996  | Hawkins |
| 6,155,812 | A |   | 12/2000 | Smith et al. |
| 6,361,731 | B1 |  | 3/2002  | Smith et al. |
| 6,942,475 | B2 |  | 9/2005  | Ensign et al. |
| 7,427,296 | B2 |  | 9/2008  | Evans |
| 7,429,346 | B2 |  | 9/2008  | Ensign et al. |
| 7,789,646 | B2 |  | 9/2010  | Haney et al. |
| 2007/0222114 | A1 | | 9/2007  | Ziran et al. |
| 2010/0102484 | A1 | * | 4/2010 | Haney et al. ............... 264/328.1 |

* cited by examiner

*Primary Examiner* — Joseph S Del Sole
*Assistant Examiner* — John Robitaille
(74) *Attorney, Agent, or Firm* — Laurence A. Greenberg; Werner H. Stemer; Ralph E. Locher

(57) ABSTRACT

An orthopedic prosthesis mold, including a first housing defining a first cavity therein shaped to form a portion of an orthopedic prosthesis; a second housing coupled to the first housing, the second housing defining a second cavity therein shaped to form a portion of an orthopedic prosthesis; and a reinforcement element attached to at least one of the first or second housings, the reinforcement element resisting deformation of the first and second housings. The reinforcement element may include a member exterior to the first and second cavities, the member spanning across a substantial width of the prosthesis mold.

19 Claims, 12 Drawing Sheets

DISPOSABLE ORTHOPEDIC PROSTHESIS MOLD

CROSS-REFERENCE TO RELATED APPLICATION

This application is related to and claims priority to U.S. Provisional Patent Application Ser. No. 61/472,498, filed Apr. 6, 2011, entitled DISPOSABLE ORTHOPEDIC PROSTHESIS MOLD, the entirety of which is incorporated herein by reference.

STATEMENT REGARDING FEDERALLY SPONSORED RESEARCH OR DEVELOPMENT n/a

FIELD OF THE INVENTION

The present invention relates to orthopedic prostheses and methods and systems for the manufacture thereof.

BACKGROUND OF THE INVENTION

A healthy knee joint is able to withstand great forces that are exerted as the knee flexes and extends and supports the weight of the body. However, when the knee joint becomes diseased, damaged or is otherwise unable to withstand the forces required of that joint, it may become necessary to reconstruct or replace the knee joint. When replacement is necessary, the natural knee joint is replaced with a prosthetic knee joint. A typical knee joint prosthesis includes a femoral component and a tibial component. During a replacement knee surgery, portions of both the tibia and femur are typically resected to allow the placement of prosthetic tibial and femoral components, which are anchored to the respective bones.

Sometimes, a small percentage of patients who undergo a total knee replacement surgery suffer from infections in the knee joint at the surgical site. To alleviate the effects of the infection, a two-stage revision of the failed knee replacement is employed. First, the failed prosthesis must be surgically removed and the site debrided and cleansed extensively in order to rid the site of the infection. Before a new, permanent prosthesis can be placed in the old surgical site, the site must be free of infection. A temporary antibiotic-impregnated cement spacer may be used as part of the therapy to rid the site of infection. Disinfecting the site of infection may take between 6-8 weeks and up to 3-4 months in most circumstances. It is thus common for surgeons to replace the old prosthetic knee with a temporary implant, typically made of bone cement, during the 6-8 week period while the infection is cleared up and before the new prosthesis is surgically implanted. The second and final step requires a separate revision surgery to then replace the temporary implant with a permanent prosthetic implant.

In the past, surgeons have been left to their own devices when forming cement implants, including the use of negative molds. The process of making a negative mold consists of the surgeon creating a mold by inserting a portion of bone cement into a bowl or other mixing container and allowing the cement to nearly cure. Prior to complete curing of the bone cement, the surgeon inserts the articulating end of the femoral component into the bone cement to create a mold. Using that mold, the surgeon then applies an oil to the mold creating a barrier for separating the cement implant from the cement mold. After applying the oil, cement may be poured into the mold allowing it cure, after which the surgeon attaches the resulting bone cement implant onto the femur as a temporary replacement.

Other methods used in the past of forming temporary implants include surgeons creating the implant with their own hands or simply putting a block of cement between the tibia and the femur to act as a spacer. However, there are many problems associated with such methods and designs, namely increased surgical time due to the preparation and formation time needed for creating the implant. Particular problems associated with the block or spacer method include completely immobilizing the knee in an extended position, after surgery, for the entire 6-8 week period, which in turn leads to soft tissue damage and further complicates the revision surgery. Therefore, reproducing the knee joint using temporary implants that simulate the natural tibial and femoral components of the knee joint is much more desirable because it permits the patient to move his/her leg through a minimal range of motion. The range of motion, while limited, significantly increases the patient's comfort over the 6-8 week period allowing the patient to bend his/her knee for sitting in a chair or for riding in a car and also increases the ease of the revision surgery because the soft tissue has not been damaged to the same extent as when the knee is completely immobilized.

Attempts have been made in the prior art to provide alternatives to surgeons creating their own negative molds or even molding a temporary implant by hand, including the use of pre-made, disposable molds. Such attempts include several drawbacks, however. For example, there may be a need for many different sized molds to accommodate the differences in size from patient to patient. Existing molds are prone to overfilling and spillage, leading to wasted materials and a messy work area. Further, some molds require a surgeon cut the mold to remove it from the implant once cured. This scoring separation can be quite cumbersome to achieve, can result in small, contaminating particles or pieces of the mold or molded prosthesis being strewn about, as well as increasing the likelihood that the molded prosthesis itself is inadvertently cut or damaged in the process. Additionally, when a mold is filled with a curable material to make the prosthesis, the pressure inside the mold can cause the mold itself (and thus the resulting prosthesis) to deform.

In view of these drawbacks, it is desirable to provide orthopedic prosthesis molds and methods of use thereof that safeguard against overfilling, spillage and deformation, are easily separable to reveal the molded prosthesis, and provide an accurate, selectable range of molded prosthesis sizes.

SUMMARY OF THE INVENTION

The present disclosure advantageously provides orthopedic prosthesis molds and methods of use thereof that safeguard against overfilling, spillage and deformation, are easily separable to reveal the molded prosthesis, and provide an accurate, selectable range of molded prosthesis sizes. In particular, an orthopedic prosthesis mold is disclosed, including a first housing defining a first cavity therein shaped to form a portion of an orthopedic prosthesis; a second housing coupled to the first housing, the second housing defining a second cavity therein shaped to form a portion of an orthopedic prosthesis; and a reinforcement element attached to at least one of the first or second housings, the reinforcement element resisting deformation of the first and second housings. The reinforcement element may include a member exterior to the first and second cavities, the member spanning across a substantial width of the prosthesis mold. The mold may include a plurality of reinforcement elements vertically spaced along the prosthesis mold. The first and second cavities may each have a concave shape, and the reinforcement element may span an interior of the concave shape exterior to the first and second cavities. At least one of the first and second cavities may define an anterior portion and a posterior portion shaped to form a femoral knee joint prosthesis, and the reinforcement element may extend between the anterior and posterior portions. The first housing may define an injection port, and the mold may include an injection port cap releasably engageable with the injection port to seal the injection port, where the injection port cap may include an indicia on a surface thereof that is positionable within the first cavity and/or a cutting edge or surface. The first housing may define a plurality of vent ports, and the mold may include a plurality of vent caps positionable to cover the vent ports, where at least one vent cap includes a cutting surface. The mold may include a connecting element releasably engageable with the first and second housings, where the connecting element prevents separation of the first housing from the second housing. The connecting element may include a strap circumscribing an exterior of the first and second housings and/or a plurality of releasably engageable portions positionable around an exterior of the first and second housings. The first and second housings may each define a protruding shoulder, and the connecting element may define a recess engageable with the shoulders.

An orthopedic prosthesis mold is provided, including a first housing defining a cavity therein shaped to create a portion of an orthopedic prosthesis; a second housing defining an injection port and a cavity therein shaped to create a portion of an orthopedic prosthesis, where the second housing is at least partially slidably positionable within the first housing; and a connecting element releasably engageable to an exterior of the first housing, where the connecting element is releasably engageable to the second housing at a plurality of positions to prevent separation of the first housing from the second housing. The first and/or second housing may include indicia corresponding to a dimension of a prosthesis. The connecting element may include a plurality of releasably engageable portions. The first housing may define an aperture therein, and the connecting element may define a protrusion passable through the aperture to engage the second housing.

A method of creating an orthopedic prosthesis is provided, including providing a first housing having a cavity therein shaped to create a portion of an orthopedic prosthesis and a second housing defining an injection port and a cavity therein shaped to create a portion of an orthopedic prosthesis, where the second housing includes a plurality of indicia indicating a plurality of dimensions for an orthopedic prosthesis; slidably positioning at least a portion of the second housing into the first housing to a preselected position indicated by the indicia; immovably securing the first housing to the second housing with a connecting element; and injecting a curable material into the injection port of the second housing. The connecting element may circumscribe an exterior of the first housing, and engage the second housing through an aperture in the first housing.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION OF THE INVENTION

Figure 1:
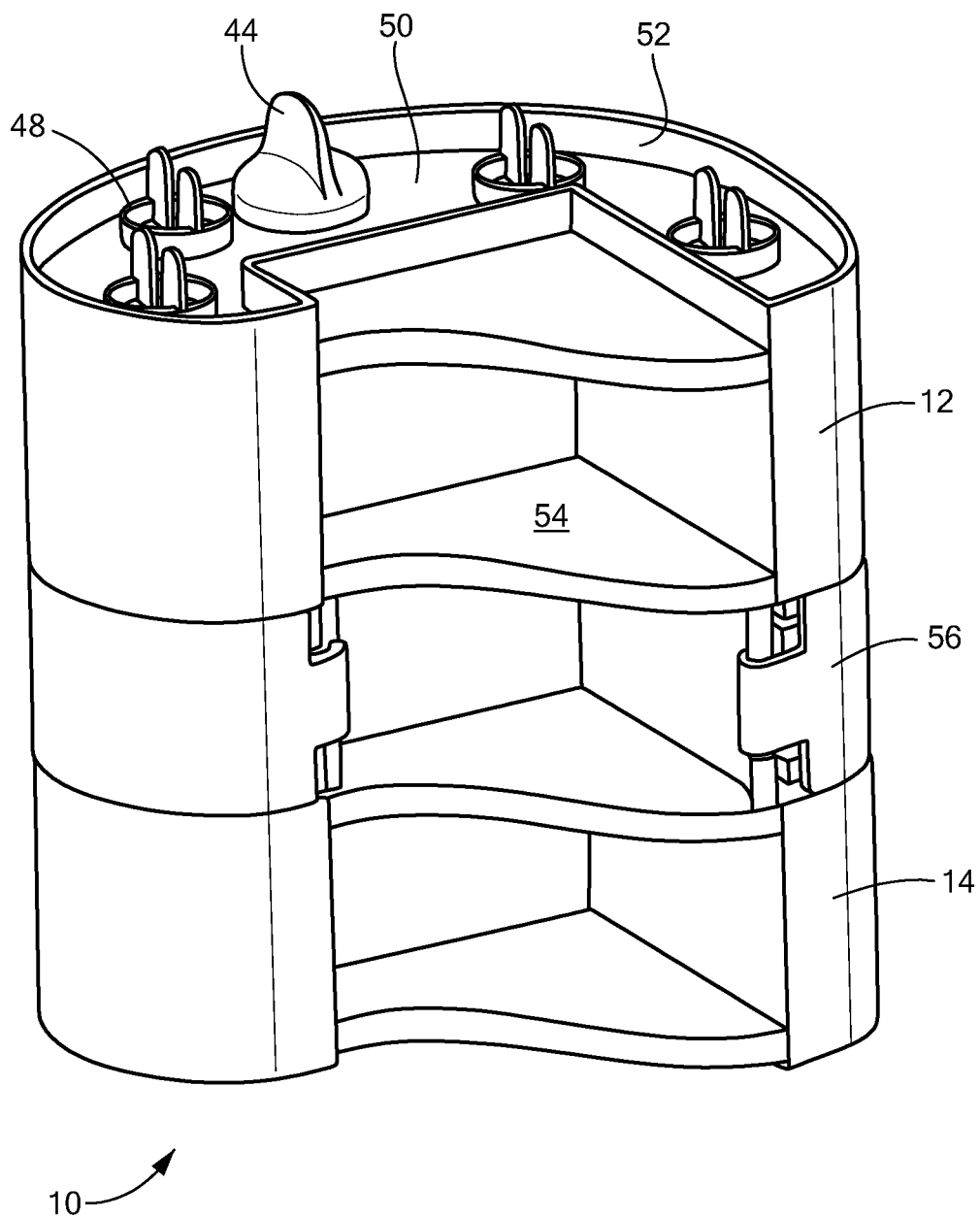
FIG. 1 is an illustration of a perspective view of an example of an orthopedic prosthesis mold constructed in accordance with the principles of the present invention.
Figure 2:
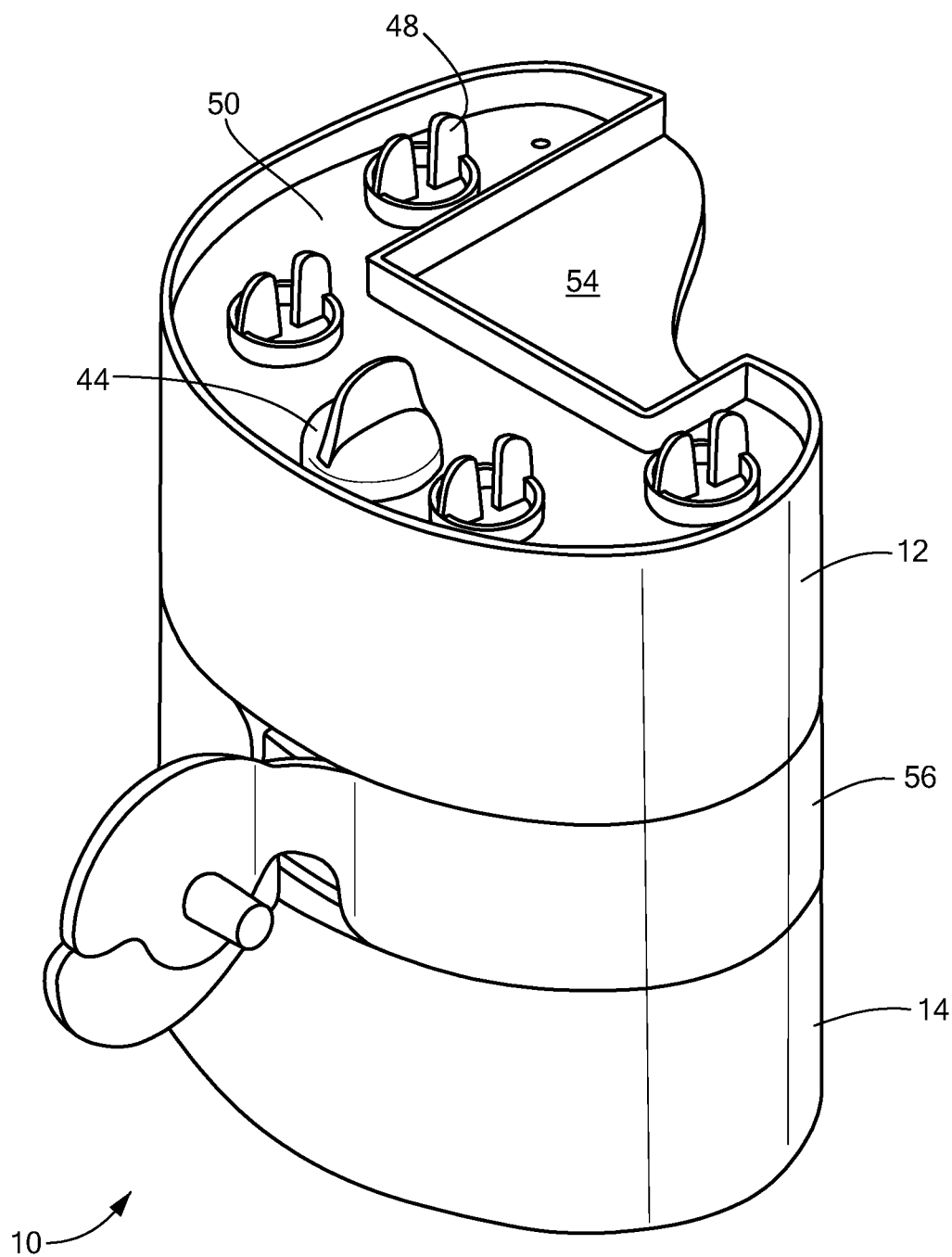
FIG. 2 is an additional illustration of a perspective view of the orthopedic prosthesis mold of FIG. 1.

The present invention provides orthopedic prosthesis molds and methods of use thereof that safeguard against overfilling, spillage and deformation, are easily separable to reveal the molded prosthesis, and provide an accurate, selectable range of molded prosthesis sizes. Referring now to the drawing figures in which like reference designations refer to like elements, an example of an orthopedic prosthesis mold constructed in accordance with principles of the present invention is shown in FIGS. 1-4 and generally designated as "10."

Figure 3:
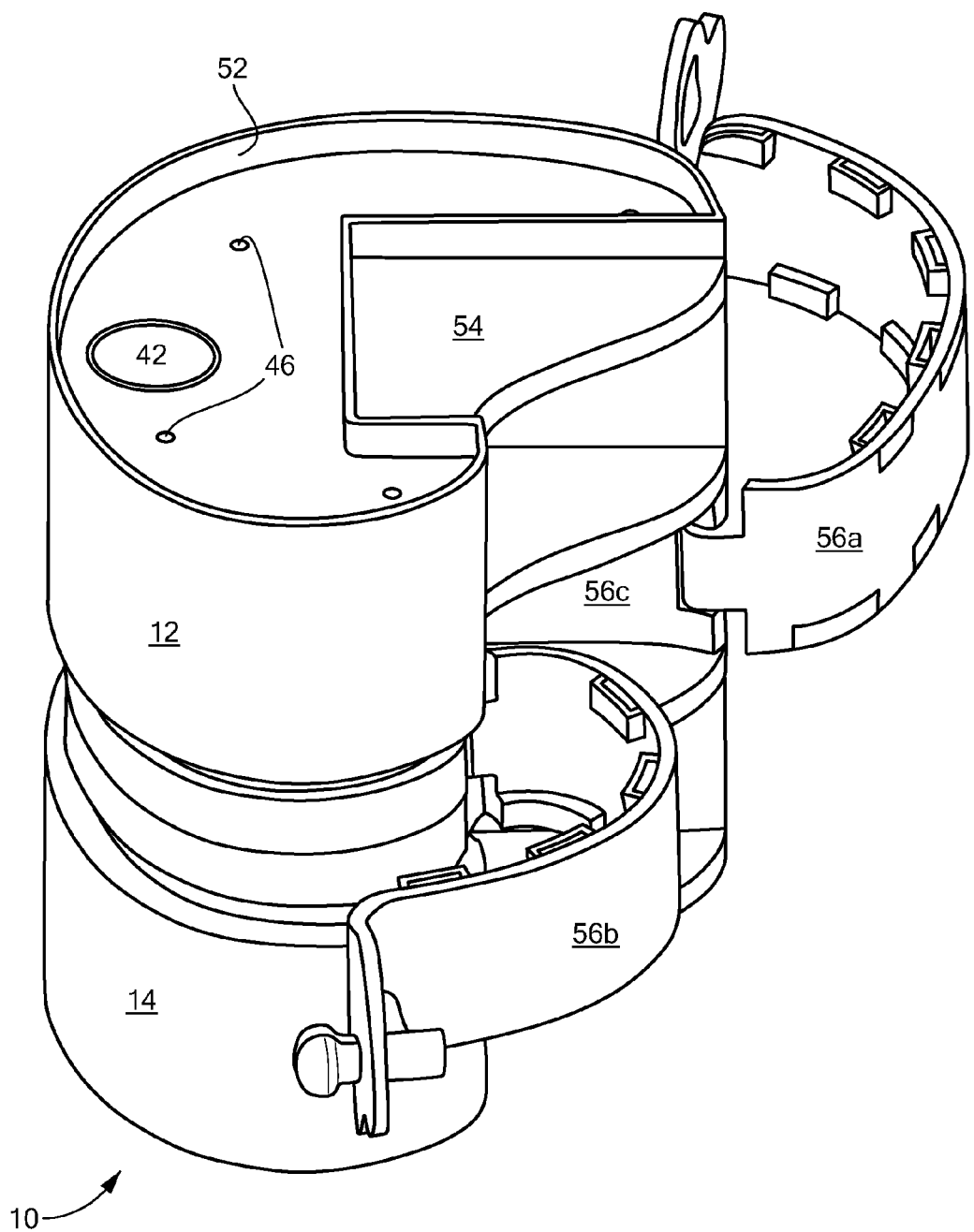
FIG. 3 is an additional illustration of a perspective view of the orthopedic prosthesis mold of FIG. 1.
Figure 4:
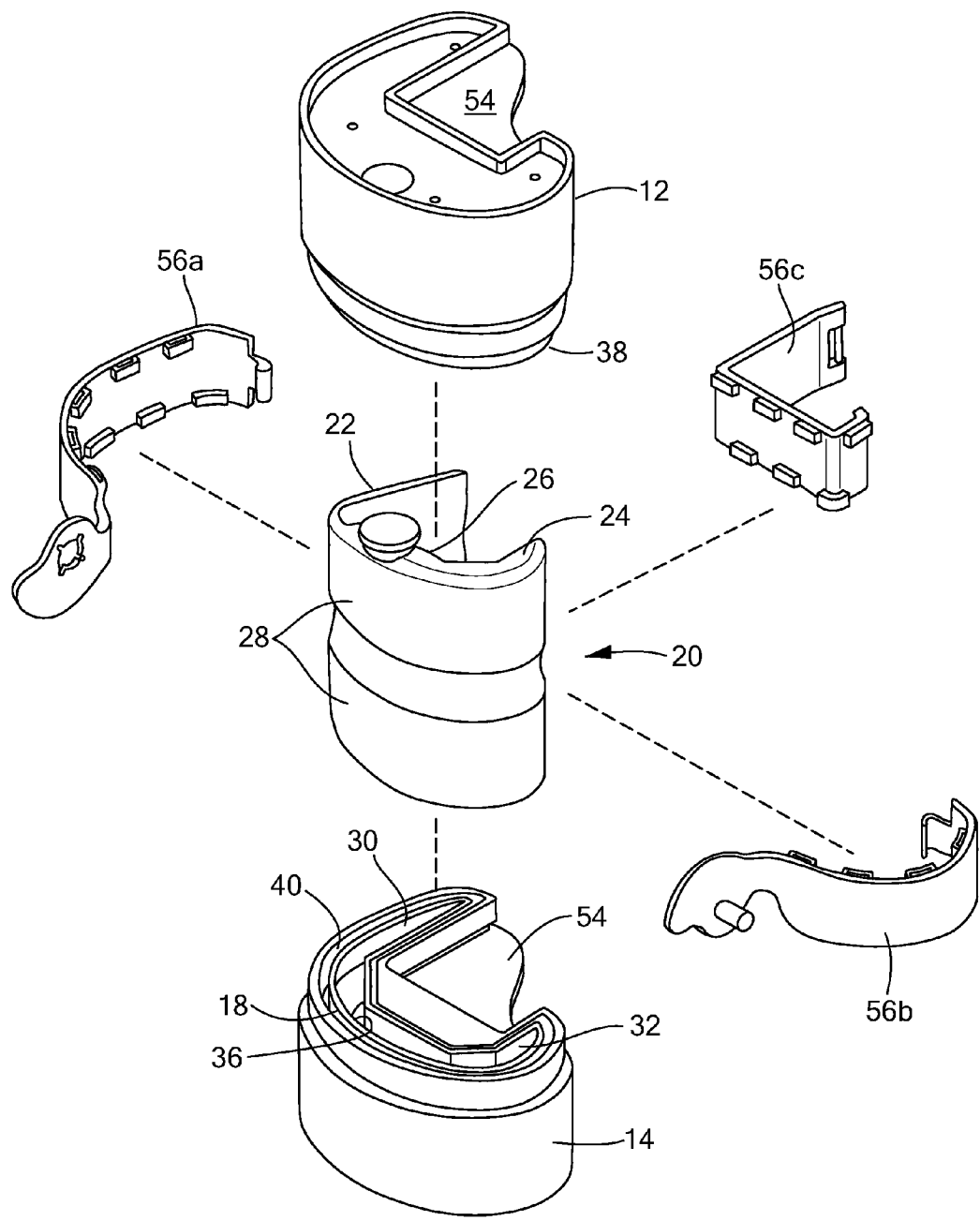
FIG. 4 is an exploded assembly view of the orthopedic prosthesis mold of FIG. 1.
Figure 6:
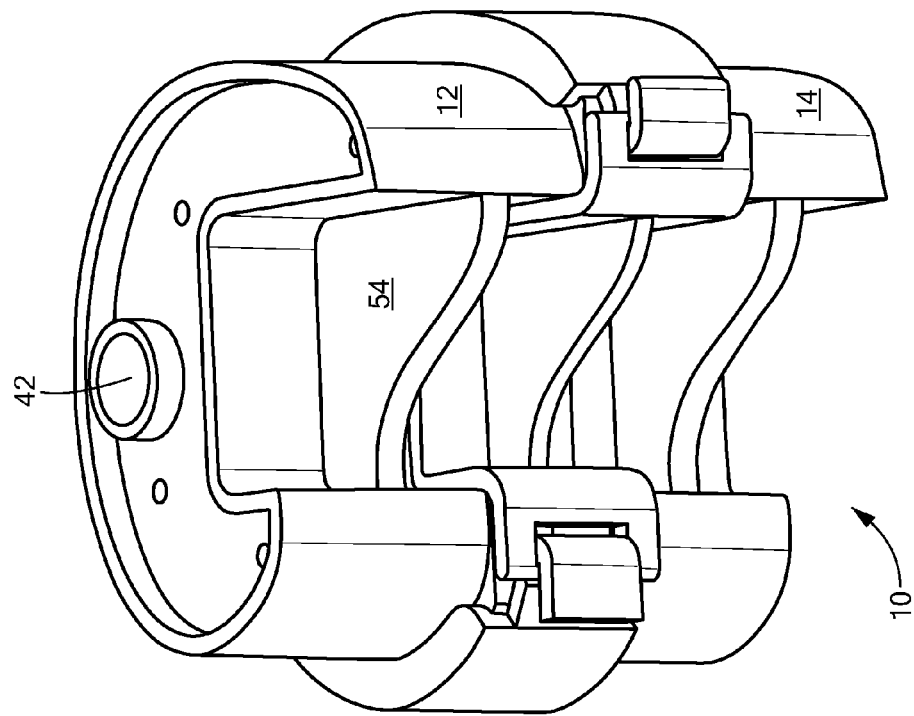
FIG. 6 is an additional illustration of a perspective view of the orthopedic prosthesis mold of FIG. 5.
Figure 5:
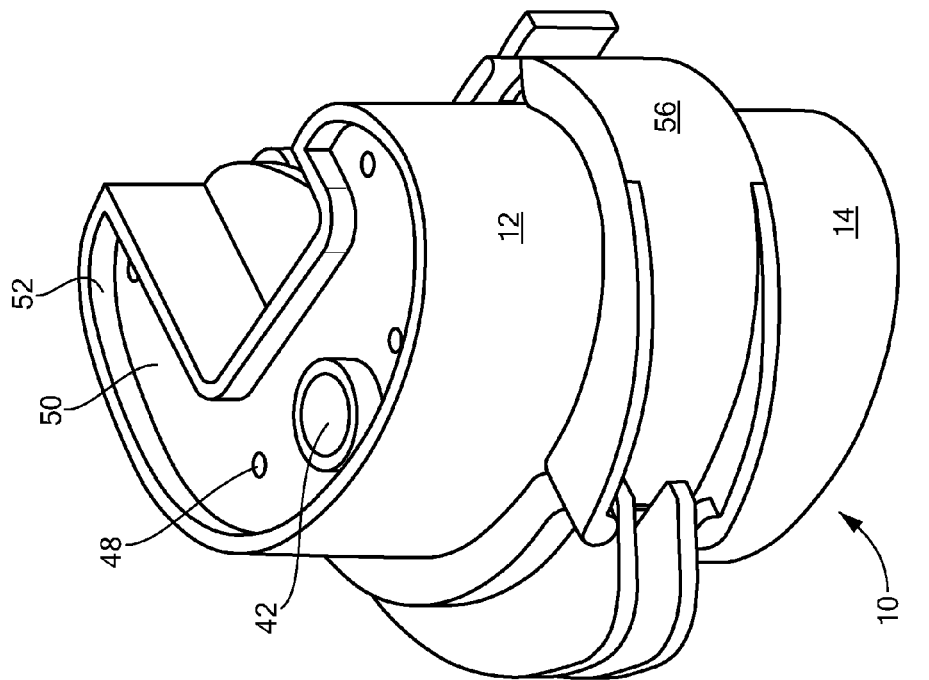
FIG. 5 is an illustration of a perspective view of another example of an orthopedic prosthesis mold constructed in accordance with the principles of the present invention.
Figure 7:
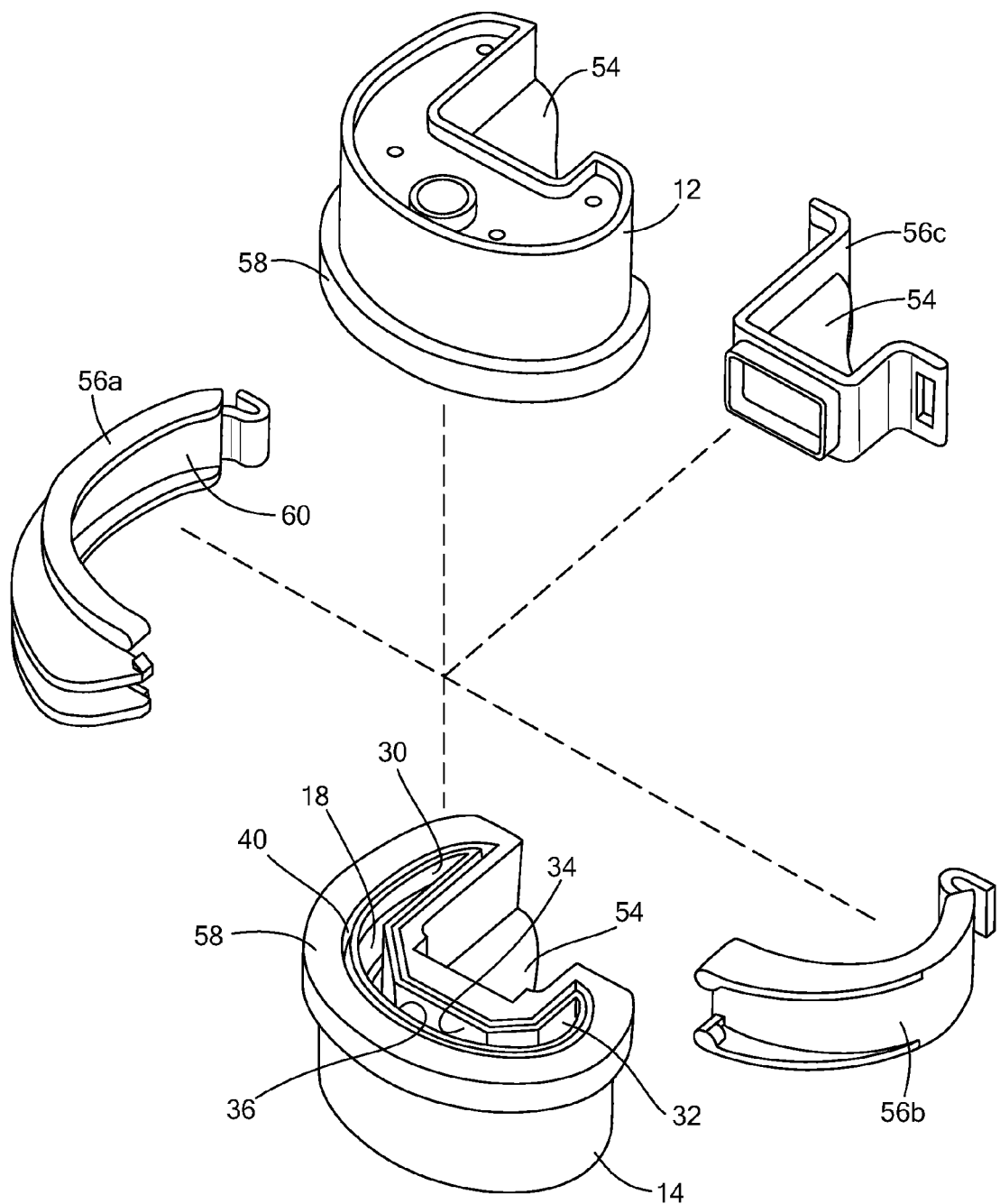
FIG. 7 is an exploded assembly view of the orthopedic prosthesis mold of FIG. 5.
Figure 8:
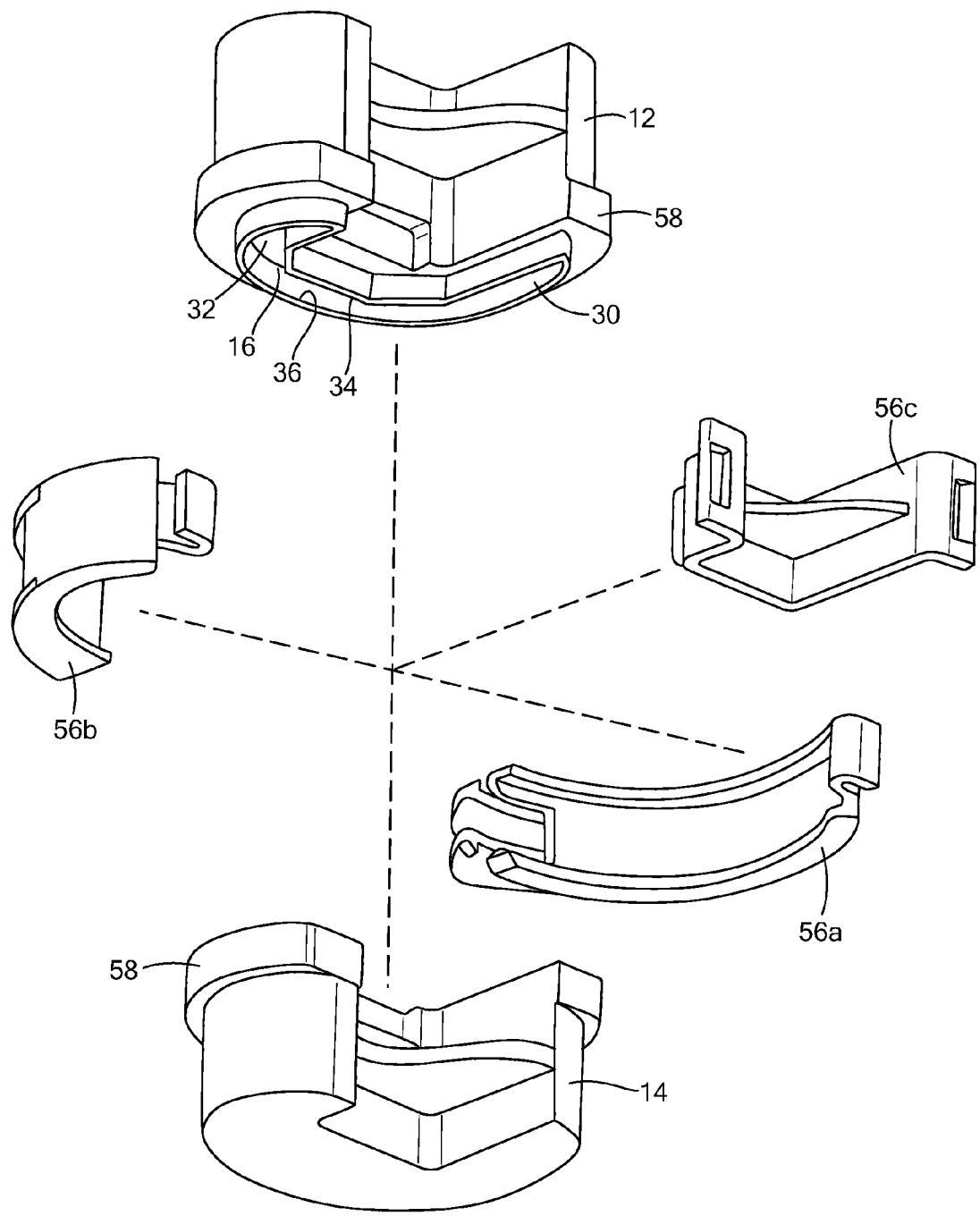
FIG. 8 is another exploded assembly view of the orthopedic prosthesis mold of FIG. 5.

The mold 10 generally includes a first housing or body 12 and a second housing or body 14 releasably engageable with the first housing. The first and second housings define cavities therein sized and shaped to produce an orthopedic prosthesis, such as that of a femoral and/or tibial knee joint component. For example, the first housing 12 may define or include a first cavity 16 therein for receiving a curable material to be formed or shaped into at least a portion of an orthopedic prosthesis. The second housing 14 may include a second cavity 18 for receiving a curable material to be formed or shaped into at least a portion of an orthopedic prosthesis. The second cavity 18 may be positional adjacent to and/or substantially congruous with the first cavity 16 when the first and second housings are engaged or coupled to one another to cooperatively from a substantially continuous prosthesis. As shown in FIG. 4, the first and second cavities of the first and second housings may from a femoral orthopedic prosthesis 20 for a knee joint. The prosthesis 20 may generally include or define an anterior portion 22 (which will be towards the anterior or front portion of the knee when implanted), a posterior portion 24 (which will be towards the back or posterior portion of the knee when implanted), and a femoral cavity or surface 26 that will couple to a portion of a femur when implanted. The prosthesis 20 may generally define a concave or crescent-shaped cross-section, where the femoral cavity or surface 26 lies within an interior of the concavity. The prosthesis 20 may also include medial and lateral condylar portions 28 on an exterior portion of the prosthesis 20 (opposite the femoral cavity) that provide bearing surfaces to contact and articulate with a tibial component or prosthesis of the knee joint when implanted. To form the illustrated prosthesis 20, the first and second cavities each include an anterior portion 30, posterior portion 32, femoral cavity or surface portion 34, and condylar portions 36 sized and shaped to form the respective, resulting features of the prosthesis 20. The mold in FIGS. 1-4 is illustrated as a femoral prosthesis mold, but it is also contemplated that the features described herein may be provided for a mold sized and shaped to form a tibial component of a knee joint, or other orthopedic prostheses.

The first and second housings 12, 14 may define one or more grooves, detents, lips, or other mating features complimentary to each other to aid in aligning and/or securing the components to one another, and to further resist separation when under pressure from injection of material into the mold and/or expansion or curing of an injected material. For example, as shown in FIG. 4, the first housing 12 may define a protruding tongue 38 on its lower end that is complementary and securely positionable within a groove or well 40 circumscribing a substantial portion of an upper end of the second housing 14. Providing such matable lock-and-key features provides increased resistance to separation between the housings, as well as reducing the likelihood of leakage at the coupling points between the first and second housings.

The first housing 12 may define an injection opening 42 in communication with the first cavity 16 to allow the mold 10 to be filled with a curable material to form the prosthesis 20. An injection opening cap or cover 44 may also be included. The injection opening cap 44 may include a stamping component or indicia that imprints the injected molding material within the first and second cavities prior to curing. This allows the resulting prosthesis to have custom markings identifying the patient, infused pharmacological information, traceability information (lot number, manufacturing date, etc.), or the like. The injection cap 44 may further include a cutting surface or edge to remove, debride, or otherwise remove excess portions of the molded prosthesis once its cured.

The first housing 12 may further define one or more vents 46 in an upper surface thereof to allow air pockets to escape, as well as provide an exit or spillway for excess material. One or more vent caps 48 may be provided to cover the vents. The vent caps 48 may include one or more serrations or cutting surfaces to excise or otherwise remove a vent flash, excess material, or unwanted protrusion from the cured prosthesis. This reduces or altogether eliminates the need to use a scalpel or secondary cutting instrument to smooth out or remove excess molded material prior to insertion or use of the implant. In addition, the first housing 12 may define a reservoir 50 surrounding or enclosing the one or more vents 46 and/or injection opening 42 to contain excess material. In a particular example, the first housing 12 may define a rim or wall 52 surrounding the vents 46 and/or injection opening 42.

The mold 10 may further define or include one or more reinforcement elements or ribs 54 coupled to the first and/or second housings 12, 14. The reinforcement elements 54 provide rigidity and structural reinforcement to resist pressure from an injected and curing material within the mold 10. Such forces often cause molds to warp or deform from their originally-intended shape, resulting in a deformed or warped prosthesis. The reinforcement elements 54 resist such deformation and thus, decrease the likelihood that a formed prosthesis will have to be discarded as defective. The reinforcement elements 54 may include a member exterior to the first and second cavities that spans across a substantial width of the prosthesis mold 10. Additionally and/or alternatively, the reinforcement elements 54 may span an interior of the concave shape defined by of the first and second cavities (but reside exterior to the cavities and thus not affect the shape of the prosthesis—for example, the reinforcement element may be coupled to an exterior surface of the first and/or second housings). In an example where the first and second cavities define anterior and posterior portions 30, 32 corresponding to anterior and posterior portions 22, 24 of a femoral orthopedic prosthesis, the reinforcement element 54 may extend between the anterior and posterior portions 30, 32 of the first and/or second cavities. The reinforcement elements 54 may also be vertically spaced along a height of the prosthesis mold.

The first and second housings 12, 14 may be releasably secured to one another by a selectively-releasable strap or connecting element 56 engageable with both the first and second housings to either secure the housings together or to facilitate their separation. The connecting element 56 may provide added rigidity and resistance to expansion or separation of the first and second housings 12, 14 when the mold 10 is injected with a molding material. For example, the connecting element 56 may be constructed from a substantially rigid plastic or polymer, while the first and second housings may be made from a more pliable substance, such as silicone.

The connecting element 56 may generally include a plurality of releasably interconnected portions. For example, the connecting element may include a first portion 56a and a second portion 56b movably and/or pivotably coupled to a third portion 56c. For example, the third portion 56c may define a hinge coupling with each of the first and second portions 56a, 56b to allow the first and second portions to be opened and disengaged from the first and second housings 12, 14, as shown in FIG. 3. The hinge coupling may include a living hinge, a detachable or pin-based hinge, or other suitable pivotable coupling or structure. The third portion 56c may further define one or more protrusions or other complimentary mating or positioning features aiding in its alignment, positioning, and/or securement to the first and second housing. The first and second portions may also be releasably engageable with one another in a closed position about the first and second housings through a locking tab or other releasably engageable mechanism.

Now referring to FIGS. 5-8, another example of the mold 10 is shown. The mold includes first and second housings 12, 14, first and second cavities 16, 18, reinforcement elements 54, connecting elements 56 and other features similar to those described above with respect to the example shown in FIGS. 1-4. In addition, the mold 10 may include a shoulder 58 protruding from the first and/or second housings. The connecting element 56 may include a recess 60 positionable on or matable to the shoulder. When the connecting element 56 is coupled to the first and second housings 12, 14, the shoulder 58 is captured or received within the recess 60, and the connecting element 56 thus prevents the separation of the first and second housings.

Now turning to FIGS. 9-13, another example of an orthopedic prosthesis mold 62 is shown. The mold 62 in FIGS. 9-13 is illustrated as a tibial prosthesis mold, but it is also contemplated that the features described herein may be provided for a mold sized and shaped to form a femoral component of a knee joint or other orthopedic prostheses. Similar to the mold 10 shown in FIGS. 1-8, the mold 62 includes a first housing 64 releasably coupled to a second housing 66 having an injection port 67, and secured by one or more portions of a connecting element 68. The first and/or second housings 64, 66 may include one or more vents (not shown), vent caps, and the like, similar to the examples shown in FIGS. 1-8. In this example, at least a portion of the second housing 66 may be slidably positionable within the first housing 64, and may be secured in any one of a plurality of selectable positions with respect to the first housing to provide a selectable range of resulting prosthesis sizes.

Figure 9:
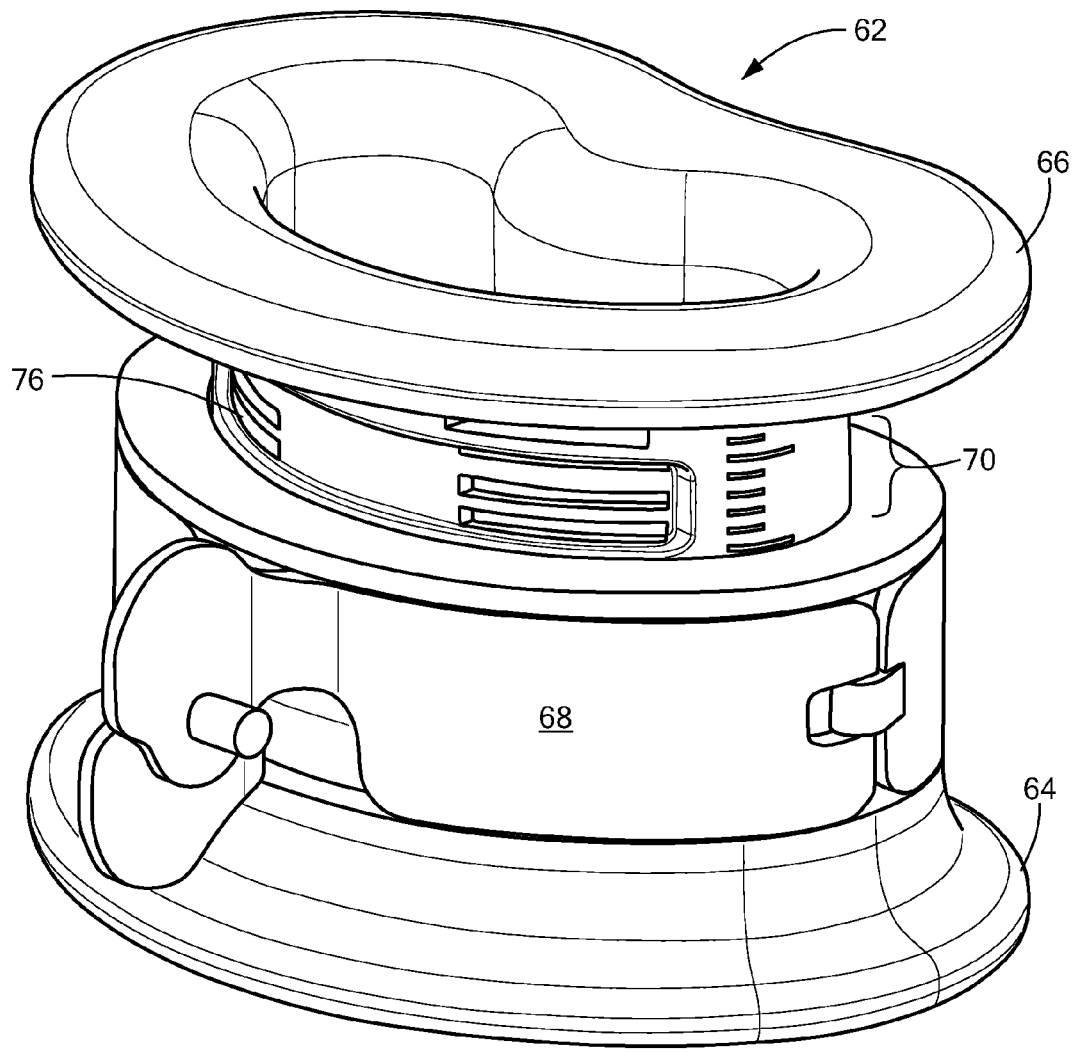
FIG. 9 is an illustration of a perspective view of another example of an orthopedic prosthesis mold constructed in accordance with the principles of the present invention.
Figure 10:
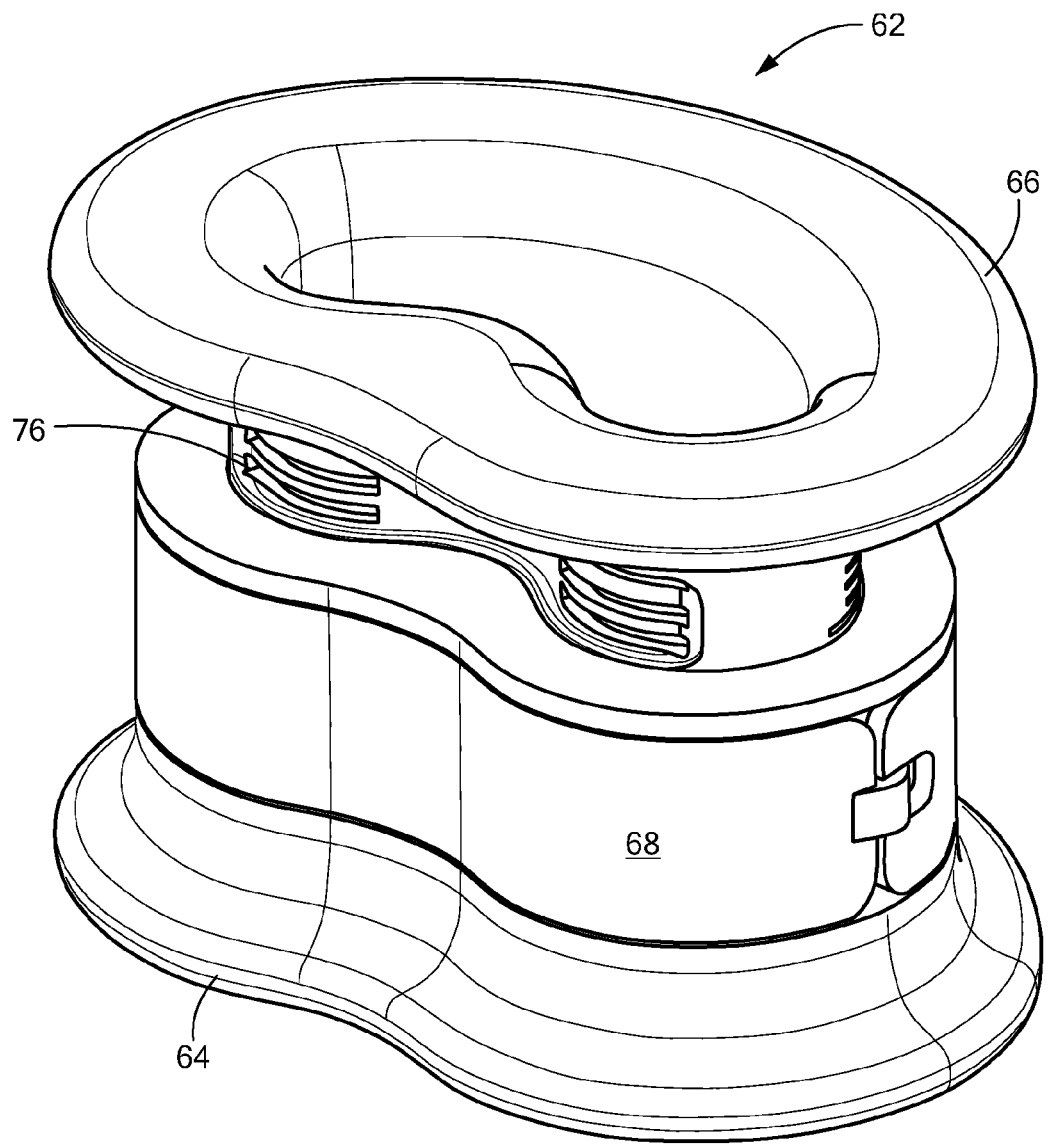
FIG. 10 is an additional illustration of a perspective view of the orthopedic prosthesis mold of FIG. 9.
Figure 11:
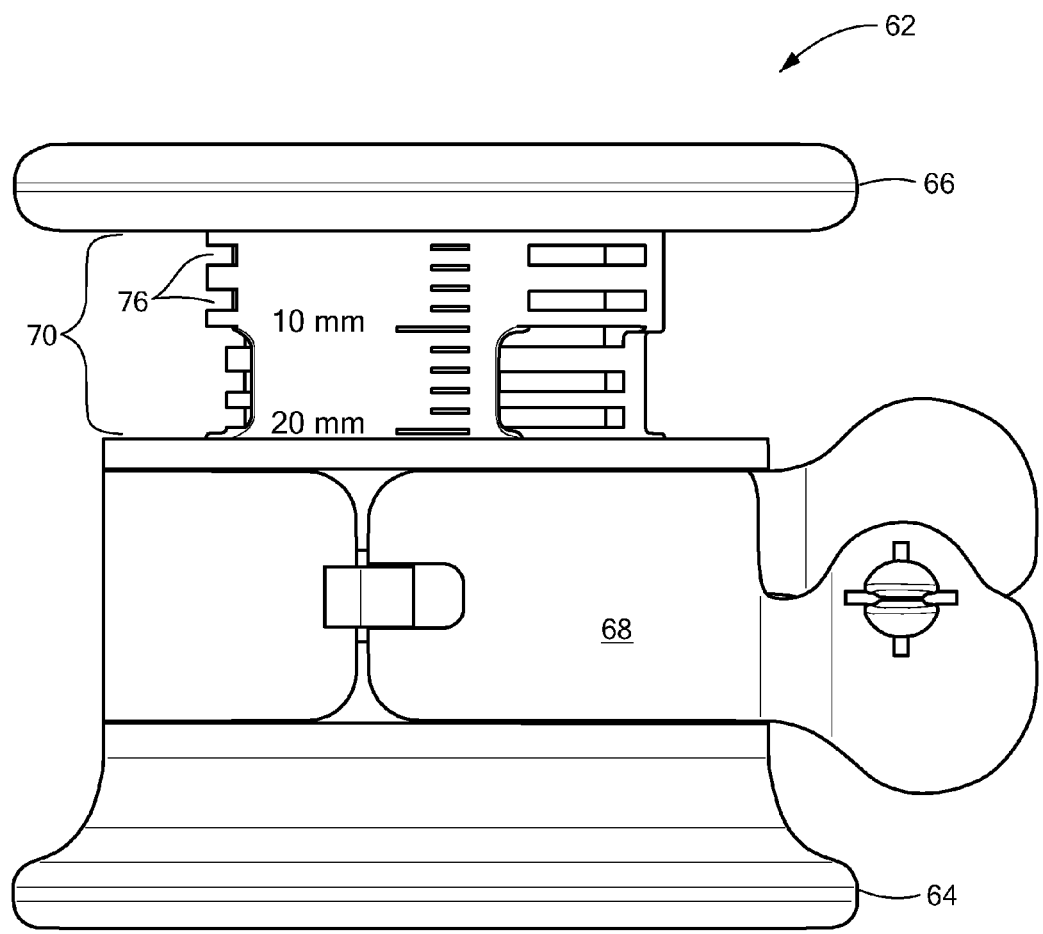
FIG. 11 is a side view of the orthopedic prosthesis mold of FIG. 9.
Figure 12:
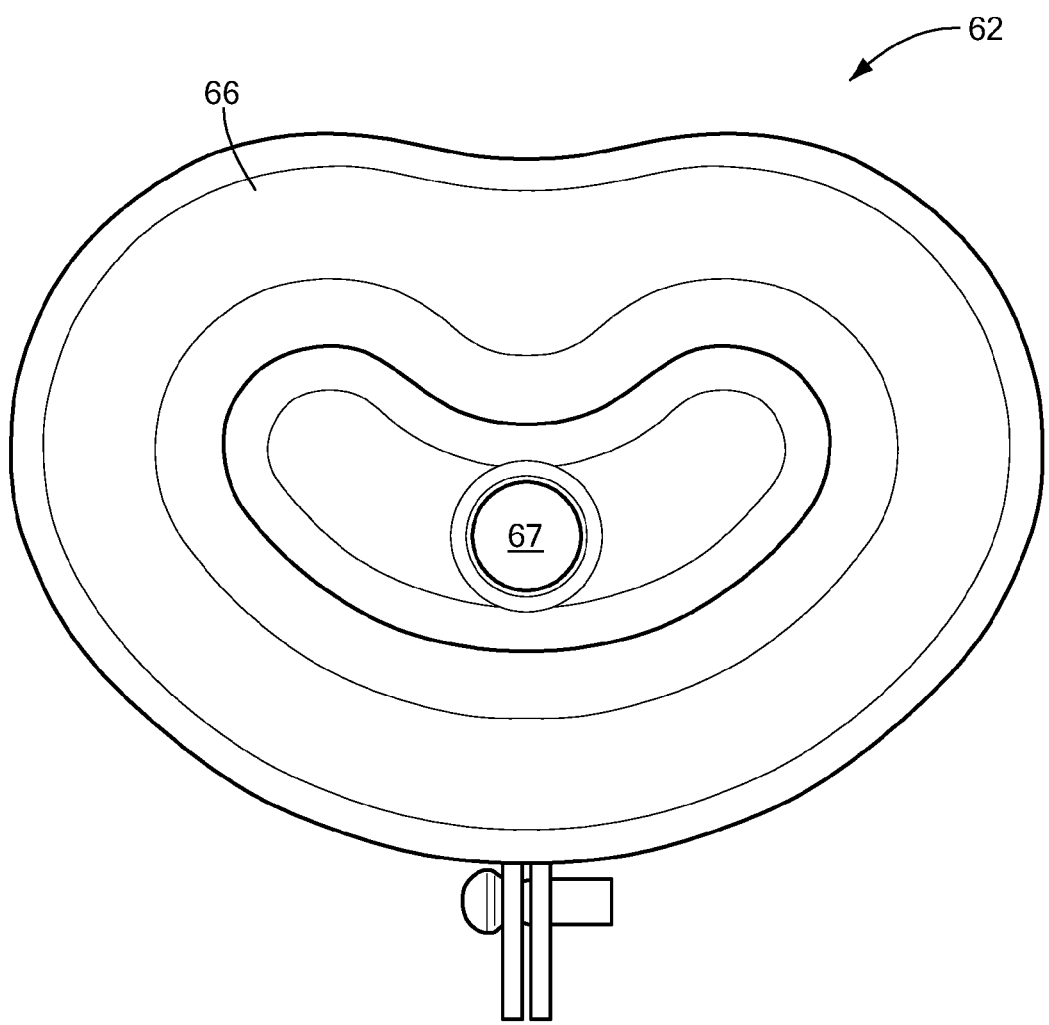
FIG. 12 is a top view of the orthopedic prosthesis mold of FIG. 9.
Figure 13:
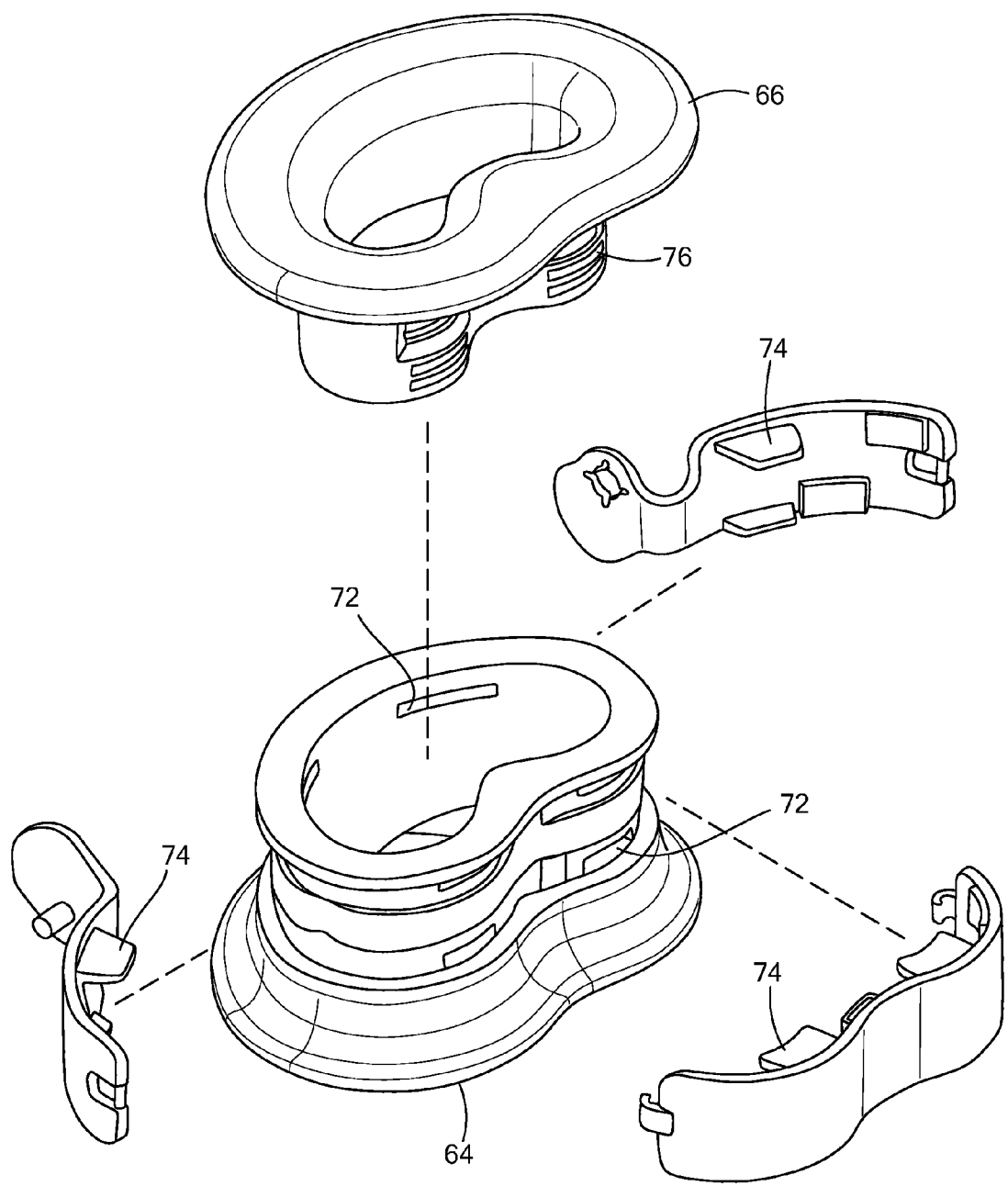
FIG. 13 is an exploded assembly view of the orthopedic prosthesis mold of FIG. 9.

The first or second housing 64, 66 may include a scale or sizing indicia 70 to allow a physician to "dial-in" the desired prosthesis size to be formed from the mold. For example, the scale 70 may be visible on an exterior surface of the second housing 66 for ease of visibility to a user, as shown in FIGS. 9-11. The exterior markings provide ease of visibility to a user, while also ensuring that precisely the selected size results, because the first and second housings can be secured in the selected position. This is in direct contrast to existing molds having an interior scale that a physician has to approximate, and then not overfill. The first and second housings may further include flared endpoints, providing easy-handling and graspable surfaces when selecting the desired prosthesis size.

The connection element 68 may be engageable with both the first and second housings to secure a selected, relative position between the first and second housings, and thus a resulting prosthesis size or shape. For example, the connection element 68 may be positionable around an exterior of the first housing 64. The first housing 64 may define or include one or more apertures 72 therein. The connecting element 68 may include one or more protrusions 74 positionable through the apertures 72 in the first housing. The protrusions 74 of the connecting element 68 may further engage one or more slots 76 on the second housing 66 to secure the parts of the mold 62 in place.

In an exemplary method of use of the molds provided herein, the first and second housings may be coupled to one another at least in part by the connecting element. Where the first and second housings provide for a selectable range of resulting prosthesis sizes, the housings may first be positioned as desired with respect to one another using the indicia or scale provided on the first and/or second housings. Once the first and second housings have been secured in their desired positions using the connection element, a molding substrate may be injected or otherwise introduced into the cavities of the first and second housings. The molding substrate may include a curable or other substance providing the desired structural or material characteristics of a resulting prosthesis. Once the desired amount of substrate has been introduced into the cavities, the injection port cap and/or vent caps may be placed over the injection port and/or vents, respectively. Once the material has cured or has otherwise reached a suitable state, the injection cap and/or the vent caps may be removed from the mold and any overflow or excess material may removed using the cutting edges or surfaces of the respective caps or covers. The connecting element may subsequently be released and detached from the first and second housings to allow the first and second housings to be separated. The prosthesis may then be removed from the first and second housings for implantation.

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the invention. For example, though tibial and femoral prosthesis shapes are illustrated, other shapes may be provided for as well. A variety of modifications and variations are possible in light of the above teachings without departing from the scope and spirit of the invention, which is limited only by the following claims.

What is claimed is:

1. An orthopedic prosthesis mold, comprising:
    a first housing including a first cavity therein shaped to form a portion of an orthopedic prosthesis, said first cavity having a concave shape;
    a second housing coupled to the first housing, the second housing including a second cavity therein shaped to form a portion of an orthopedic prosthesis, said second cavity also having a concave shape;
    each of the first housing and second housing including at least one attached reinforcement rib, the reinforcement rib resisting deformation of the first and second housings; and
    wherein the at least one attached reinforcement rib of each of the first housing and second housing spans an interior of the concave shape exterior to each of the first and second cavities.

2. The orthopedic prosthesis mold of claim 1, wherein the at least one attached reinforcement rib includes a member spanning across a substantial width of the prosthesis mold.

3. The orthopedic prosthesis mold of claim 1, further comprising a plurality of reinforcement ribs vertically spaced along the prosthesis mold.

4. The orthopedic prosthesis mold of claim 1, wherein at least one of the first and second cavities defines an anterior portion and a posterior portion shaped to form a femoral knee joint prosthesis, and wherein the at least one attached reinforcement rib of the at least one of the first and second cavities extends between the anterior and posterior portions.

5. The orthopedic prosthesis mold of claim 1, wherein the first housing defines an injection port.

6. The orthopedic prosthesis mold of claim 5, further comprising an injection port cap releasably engageable with the injection port to seal the injection port.

7. The orthopedic prosthesis mold of claim 6, wherein the injection port cap includes an indicia on a surface thereof that is positionable within the first cavity.

8. The orthopedic prosthesis mold of claim 5, wherein the first housing defines a plurality of vent ports.

9. The orthopedic prosthesis mold of claim 8, further comprising a plurality of vent caps positionable to cover the vent ports, wherein at least one vent cap includes a cutting surface.

10. The orthopedic prosthesis mold of claim 1, further comprising a connecting element releasably engageable with the first and second housings, the connecting element preventing separation of the first housing from the second housing.

11. The orthopedic prosthesis mold of claim 10, wherein the connecting element includes a strap circumscribing around an exterior of the first and second housings.

12. The orthopedic prosthesis mold of claim 10, wherein the connecting element includes a strap formed of a plurality of releasably engageable portions and positionable around an exterior of the first and second housings.

13. The orthopedic prosthesis mold of claim 10, wherein the first and second housings each define a protruding shoulder, and wherein the connecting element defines a recess engageable with the shoulders.

14. An orthopedic prosthesis mold, comprising:
a first housing including a first cavity in said first housing, said first cavity shaped to create a portion of an orthopedic prosthesis;
a second housing including an injection port and a second cavity in said second housing, said second cavity shaped to create a portion of an orthopedic prosthesis, wherein the second housing is at least partially slidably positionable within the first housing to a selected position; and
a connecting element including a strap releasably engageable to an exterior of the first housing to secure a relative position between the first and second housings, wherein the strap is releasably engageable to an exterior of the second housing at a plurality of positions to prevent separation of the first housing from the second housing.

15. The orthopedic prosthesis mold of claim 14, wherein the second housing includes indicia corresponding to a dimension of a prosthesis.

16. The orthopedic prosthesis mold of claim 14, wherein the strap includes a plurality of releasably engageable, pivoting portions.

17. The orthopedic prosthesis mold of claim 14, wherein the first housing defines an aperture therein, and the connecting element defines a protrusion passable through the aperture to engage the second housing.

18. A method of creating an orthopedic prosthesis, comprising:
providing a first housing including a first cavity therein shaped to create a portion of an orthopedic prosthesis and a second housing including an injection port and a second cavity therein shaped to create a portion of an orthopedic prosthesis, wherein the second housing includes a plurality of indicia indicating a plurality of dimensions for an orthopedic prosthesis;
slidably positioning at least a portion of the second housing within the first housing to a preselected position indicated by the indicia;
immovably securing a position of the first housing relative to the second housing with a connecting element strap including a strap releasably engageable to an exterior of the first housing and to an exterior of the second housing at a plurality of positions to prevent separation of the first housing from the second housing;
and injecting a curable material into the injection port of the second housing.

19. The method of claim 18, wherein the strap circumscribes around an exterior of the first housing, and engages the second housing through an aperture in the first housing.

* * * * *